United States Patent [19]

Doe, Jr.

[11] Patent Number: 4,617,136

[45] Date of Patent: Oct. 14, 1986

[54] DICOCOAMINE DERIVATIVES OF 2,5-DIMERCAPTO-1,3,4-THIADIAZOLE

[75] Inventor: Lester A. Doe, Jr., Newtown, Conn.

[73] Assignee: R. T. Vanderbilt Company, Inc., Norwalk, Conn.

[21] Appl. No.: 766,382

[22] Filed: Aug. 16, 1985

[51] Int. Cl.$^4$ .................. C10M 135/36; C07D 285/12
[52] U.S. Cl. ...................................... 252/47; 548/142
[58] Field of Search ........................... 548/142; 252/47

[56] References Cited

U.S. PATENT DOCUMENTS

| 2,719,125 | 9/1955 | Roberts | 252/46.7 |
| 2,719,126 | 9/1955 | Fields et al. | 252/47 |
| 2,765,289 | 10/1956 | Fields et al. | 252/32.7 |
| 2,781,399 | 2/1957 | Shapiro | 260/583 |
| 2,910,439 | 10/1959 | Fields | 252/46.7 |
| 3,087,932 | 4/1963 | Little | 260/302 |
| 3,923,669 | 12/1975 | Newingham et al. | 252/32.7 E |
| 3,966,623 | 6/1976 | Krug et al. | 252/47 |
| 4,104,179 | 8/1978 | Colclough | 252/32.7 E |

FOREIGN PATENT DOCUMENTS 966842  4/1975  Canada ............... 260/308.3

Primary Examiner—Donald G. Daus
Assistant Examiner—Mary E. Ceperley
Attorney, Agent, or Firm—Rasma B. Balodis

[57] ABSTRACT

This invention relates to novel dicocoamine derivatives of 2-(octyldithio)-5-mercapto-1,3,4-thiadiazole. The compounds are suitable for use as corrosion inhibitors in lubricating compositions.

3 Claims, No Drawings

4,617,136

DICOCOAMINE DERIVATIVES OF 2,5-DIMERCAPTO-1,3,4-THIADIAZOLE

BACKGROUND OF THE INVENTION

This invention concerns novel dicocoamine derivatives of 2,5-dimercapto-1,3,4-thiadiazole.

According to a particular embodiment, the invention relates to dicocoamine derivatives of 2,5-dimercapto-1,3,4-thiadiazole which possess improved corrosion resistance towards metals and lubricating compositions containing same.

Lubricants which are used for heavy duty service such as maintenance of diesel engines, internal combustion engines and the like contain a variety of additives to prevent their deterioration during use and to improve the overall performance of the lubricant. These additives can cause excessive wear of special components of the engine due to chemical reactions between the additive and the metal. Particularly detrimental are sulfur-containing additives which are widely used as extreme pressure agents and anti-oxidants. The sulfur compounds tend to corrode those metal parts which contain copper, bronze, silver and other sulfur-reactive metals.

In the past, corrosion of metals has been inhibited by adding to the lubricating composition 2,5-bis(hydrocarbyldithio)-1,3,4-thiadiazoles disclosed in U.S. Pat. No. 3,087,932 to Little and 2-hydrocarbyldithio-5-mercapto-1,3,4-thiadiazoles described in Canadian Patent No. 966,842 to Blaha.

It has now been discovered that improved corrosion protection of copper, bronze, silver and the like can be imparted to lubricating compositions by adding certain asymmetrical dicocoamine derivatives of 2,5-dimercapto-1,3,4-thiadiazole.

SUMMARY OF THE INVENTION

The present invention provides novel 2,5-dimercapto-1,3,4-thiadiazole compounds selected from the group consisting of 5-dicocoaminomethylthio-2-alkyldithio-1,3,4-thiadiazole and dicocoamine salt of 2-alkyldithio-5-mercapto-1,3,4-thiadiazole.

Another aspect of the invention provides a lubricating composition comprising a major portion of an oil of lubricating viscosity and a corrosion inhibiting amount of oil soluble 5-dicocoaminomethylthio-2-octyldithio-1,3,4-thiadiazole or dicocoamine salt of 2-octyldithio-5-mercapto-1,3,4-thiadiazole.

DETAILED DESCRIPTION OF THE INVENTION

The compounds of the invention may be prepared by a two stage oxidative coupling and condensation method.

In the first stage, 2,5-dimercapto-1,3,4-thiadiazole and alkyl monomercaptan are reacted in a solvent and in the presence of an oxidative coupling agent by oxidative coupling method as described in Canadian Pat. No. 966,842. The product, 2-alkyldithio-5-mercapto-1,3,4-thiadiazole is reacted in situ with formaldehyde and dicocoamine by a condensation reaction to form 2-alkyldithio-5-(dicocoaminomethylthio)-1,3,4-thiadiazole. Alternately, the product may be reacted with dicocamine to form the salt. A peroxy compound may be used to provide a source of oxygen for the oxidative coupling step. A particularly preferred oxidative coupling agent is hydrogen peroxide.

Mercaptans which may be used in the reaction are hydrocarbyl monomercaptans. The hydrocarbyl group is preferably an alkyl group. Particularly preferred mercaptan is n-octylmercaptan.

For preparation of the compounds of the invention, the secondary amines may be selected from dialkylamines derived from aliphatic and fatty acids of vegetable and animal origin. The fatty acid derived amines consist of mixed derivatives of varied alkyl chain length. Preferred, among others, are amines derived from coconut fatty acids. Particularly preferred is dicocoamine.

The secondary aliphatic amines may be prepared by known methods. An exemplary method involves the catalytic hydrogenation of aliphatic nitriles as described in U.S. Pat. No. 2,781,399 granted to Shapiro.

According to the reaction scheme, all reactants may be used in equimolar amounts. However, the molar ratio of the coupling agent based on the available oxygen may range from about 1.00 to about 1.50 moles per mole of thiadiazole. The monomercaptan may range from about 1.00 to 1.25 moles per mole of thiadiazole.

The fatty amine may range from about 1.0 to about 1.30 moles per mole of thiadiazole. A slight excess of the theoretical amount of fatty amine in the reaction mixture is particularly advantageous for applications in oleaginous media. The excess of fatty amine enhances the oleophilic properties of the product and renders it more soluble in oils.

The solvent may be any chemically inert solvent. Advantageously, an alcohol type solvent is selected which refluxes within the temperature range of the reaction. The desirable range is from about 70° C. to about 90° C.

The compounds of the invention impart metal corrosion inhibiting properties to natural and synthetic lubricants formulated as oils and greases. Particularly active are dicocoamine derivatives of 2-octyldithio-1,3,4-thiadiazole. The compounds either in pure form or as oil mixtures may be incorporated in any suitable lubricating media by known methods.

The base oils employed as lubricant vehicles may be natural mineral and petroleum hydrocarbon oils of suitable lubricating viscosity range as, for example, from about 45 SSU to 6000 SSU at 38° C.

Typical synthetic oils include ester-type oils as for example silicate esters and pentaerythritol esters, hydrogenated mineral oils, silicones and silanes.

The compounds may be incorporated in the lubricant in an amount effective for inhibiting metal corrosion. In many instances, an amount from about 0.1 to 1.0 percent will be sufficient. A preferred range is from about 0.1 to about 0.5 percent by weight of the total lubricating composition.

The lubricating compositions may contain other conventional additives depending on the intended use of the lubricant. For example, formulations may contain antioxidants such as metal dithiocarbamates, metal phosphorodithioates, aromatic amines; extreme pressure agents and antiwear agents such as organomolybdenum compounds; rust inhibitors such as metal salts of naphthalenesulfonic acids and benzenesulfonic acids; demulsifiers, antistatic agents and the like. The lubricating greases may contain thickening agents.

The following examples are given for the purpose of illustrating the invention and are not intended in any way to limit the invention. All percentages and parts are based on weight unless otherwise indicated.

EXAMPLE I

A two liter round bottom flask was charged with 0.600 moles n-octylmercaptan, 0.600 moles 2,5-dimercapto-1,3,4-thiadiazole and 500 ml ethanol. Then 0.600 moles hydrogen peroxide were added dropwise over a period of about half hour while maintaining the reaction at about 44° C. with the aid of a water bath. The reaction mixture was heated to reflux and maintained at about 82° C. for one hour. After cooling to 70° C., 0.723 moles dicocoamine and 0.600 moles formaldehyde were added to the mixture and refluxed for one hour.

The reaction mixture was cooled and then stripped in a rotary evaporator using aspirator vacuum to give a dark red liquid which slowly solidified. The yield was 97 percent.

EXAMPLE II

A 500 ml round bottom flask equipped with a stirrer, thermometer and a condenser was charged with 0.200 moles 2,5-dimercapto-1,3,4-thiadiazole, 0.200 moles n-octyl mercaptan and 150 ml ethanol. Then 0.200 moles hydrogen peroxide were added dropwise over a period of ¾ hour while maintaining the temperature at 30° to 40° C. with the aid of a water bath. The reaction mixture was heated to reflux and maintained at about 82° C. for one hour. After cooling to 71° C., 0.200 moles dicocoamine were added and the reaction mixture was stirred for ¼ hour. Thereafter, volatiles were removed in a rotary evaporator using aspirator vacuum. The product was filtered through a filter aid to give a clear dark red liquid which solidified to a yellowish brown solid. The yield was 95 percent.

EXAMPLE III

The compounds of the invention were evaluated as copper inhibitors by the copper strip tarnish test according to ASTM D-130. A standard copper strip was placed in a test tube containing test oil and heated on water bath at 65.5° and 121° C. for 3 hours. Thereafter the strip was evaluated for corrosion by comparing with standard ASTM copper strips, and subsequently after 8 and 24 hours.

A rating of 1A to 3B indicates slight to dark tarnish, while a rating of 4A to 4C denotes corrosion.

The test oil was a paraffin oil (Vitrea 71 manufactured by Shell Oil Company). To simulate practical lubricating applications, the test oil A was admixed with 0.01 percent sulfur. Test oil B was formulated with 5 percent commercial lubricating additive combination consisting of 30 percent sulfurized sperm oil, 40 percent sulfur-containing extreme pressure agent (Anglamol 32 manufactured by Lubrizol Corporation), 14.4 percent isooctyl acid phosphate, 10.4 percent tertiary $C_{12-14}$-alkylamine and 5.2 percent N-tallow-1,3-diaminopropane. The corrosion inhibitors of the invention were added to the test oils in the amount indicated in Table I.

The results compiled in Table I below show that compounds of the invention impart good corrosion protection in the presence of sulfur and phosphorus containing compounds. The corrosion inhibiting activity was better and for longer periods of time than that of a commercial product 2,5-di-t-octyldithio-1,3,4-thiadiazole (Amoco 150 manufactured by Amoco Chemical Company) which was used as control.

TABLE I

| | Copper Corrosion Test | | | | |
|---|---|---|---|---|---|
| | Additive, | Base Stock A | | Base Stock B | |
| Additive | Percent | Rating | Hours | Rating | Hours |
| None | — | 4C | 3 | — | |
| None | — | — | | 4C | 3 |
| Control | 0.1 | 3B | 5 | 3A | >9 |
| 5-Dicocoaminomethylthio-2-(n-octyldithio)-1,3,4-thiadiazole | 0.1 | 3B | 8 | 1B | 24 |
| Dicocoamine salt of 2-(n-octyldithio)-5-mercapto-1,3,4-thiadiazole | 0.1 | 3B | >9 | 2C | >9 |

What is claimed is:

1. A 2,5-dimercapto-1,3,4-thiadiazole compound selected from the group consisting of 5-dicocoaminomethylthio-2-(octyldithio)-1,3,4-thiadiazole and dicocoamine salt of 2-(octyldithio)-5-mercapto-1,3,4-thiadiazole.

2. A lubricating composition comprising a major part of oil of lubricating viscosity and a corrosion inhibiting amount of 5-dicocoaminomethylthio-2-(octyldithio)-1,3,4-thiadiazole.

3. A lubricating composition comprising a major part of oil of lubricating viscosity and a corrosion inhibiting amount of dicocoamine salt of 2-(octyldithio)-5-mercapto-1,3,4-thiadiazole.

* * * * *

UNITED STATES PATENT AND TRADEMARK OFFICE
CERTIFICATE OF CORRECTION

PATENT NO. : 4,617,136
DATED : Oct. 14, 1986
INVENTOR(S) : LESTER A. DOE, JR.

It is certified that error appears in the above-identified patent and that said Letters Patent are hereby corrected as shown below:

Column 1, line 65
"dicocamine" should be - - dicocoamine--;

Column 4, line 12
"phosphosphorus" should be -- phosphorus--.

Signed and Sealed this
Thirtieth Day of December, 1986

*Attest:*

DONALD J. QUIGG

*Attesting Officer*   *Commissioner of Patents and Trademarks*